(12) United States Patent
Lane

(10) Patent No.: US 7,201,771 B2
(45) Date of Patent: *Apr. 10, 2007

(54) BIOPROSTHETIC HEART VALVE

(75) Inventor: Ernest Lane, Huntington Beach, CA (US)

(73) Assignee: Arbor Surgical Technologies, Inc., Irvine, CA (US)

( * ) Notice: Subject to any disclaimer, the term of this patent is extended or adjusted under 35 U.S.C. 154(b) by 630 days.

This patent is subject to a terminal disclaimer.

(21) Appl. No.: 10/331,086

(22) Filed: Dec. 26, 2002

(65) Prior Publication Data

US 2003/0167089 A1    Sep. 4, 2003

(51) Int. Cl.
A61F 2/24     (2006.01)
(52) U.S. Cl. ...................................... 623/2.14
(58) Field of Classification Search ......... 623/2.1–2.42
See application file for complete search history.

(56) References Cited

U.S. PATENT DOCUMENTS

| | | | |
|---|---|---|---|
| 3,755,823 A | 9/1973 | Hancock | |
| 3,839,741 A | 10/1974 | Haller | |
| 3,983,581 A * | 10/1976 | Angell et al. | 623/2.15 |
| 4,164,046 A | 8/1979 | Cooley | |
| 4,259,753 A | 4/1981 | Liotta et al. | |
| 4,388,735 A | 6/1983 | Ionescu et al. | |
| 4,441,216 A | 4/1984 | Ionescu et al. | |
| 4,477,930 A | 10/1984 | Totten et al. | |
| 4,666,442 A | 5/1987 | Arru et al. | |
| 4,687,483 A | 8/1987 | Fisher et al. | |
| 4,692,164 A * | 9/1987 | Dzemeshkevich et al. | 623/2.14 |
| 4,705,516 A | 11/1987 | Barone et al. | |
| 4,725,274 A | 2/1988 | Lane et al. | |
| 4,790,843 A | 12/1988 | Carpentier et al. | |
| 4,816,029 A | 3/1989 | Penny, III et al. | |
| 4,851,000 A | 7/1989 | Gupta | |
| 4,892,541 A | 1/1990 | Alonso | |
| 5,026,391 A | 6/1991 | McQueen et al. | |
| 5,032,128 A | 7/1991 | Alonso | |
| 5,037,434 A | 8/1991 | Lane | |
| 5,147,391 A | 9/1992 | Lane | |
| 5,449,384 A | 9/1995 | Johnson | |
| 5,469,868 A | 11/1995 | Reger | |
| 5,549,665 A | 8/1996 | Vesely et al. | |
| 5,549,666 A | 8/1996 | Hata et al. | |
| 5,713,953 A * | 2/1998 | Vallana et al. | 623/2.15 |
| 5,716,417 A * | 2/1998 | Girard et al. | 623/2.38 |
| 5,861,028 A | 1/1999 | Angell | |
| 5,876,436 A | 3/1999 | Vanney et al. | |
| 5,910,170 A | 6/1999 | Reimink et al. | |
| 5,928,281 A | 7/1999 | Huynh et al. | |
| 5,935,163 A | 8/1999 | Gabbay | 623/2 |

(Continued)

FOREIGN PATENT DOCUMENTS

EP    1088529    4/2001

(Continued)

*Primary Examiner*—Suzette Gherbi
(74) *Attorney, Agent, or Firm*—Vista IP Law Group LLP; William A. English

(57) ABSTRACT

A trileaflet biological prosthetic heart valve (11, 41) comprising a thin, rigid annular outer frame (25, 43) which supports three elastic, laminated spring inner frames (18, 57) which in turn provide consistent geometric form and structure for attachment of tissue leaflets (15, 71).

16 Claims, 6 Drawing Sheets

U.S. PATENT DOCUMENTS

| | | |
|---|---|---|
| 5,984,959 A | 11/1999 | Robertson et al. |
| 6,074,417 A | 6/2000 | Peredo ......................... 623/2 |
| 6,102,944 A | 8/2000 | Huynh et al. ............... 623/2.14 |
| 6,168,614 B1 | 1/2001 | Andersen et al. |
| 6,254,636 B1 | 7/2001 | Peredo |
| 6,270,527 B1 | 8/2001 | Campbell et al. .......... 623/2.18 |
| 6,283,995 B1 | 9/2001 | Moe et al. ................. 623/2.19 |
| 6,319,281 B1 | 11/2001 | Patel |
| 6,322,588 B1* | 11/2001 | Ogle et al. ................. 623/1.46 |
| 6,338,740 B1 | 1/2002 | Carpentier |
| 6,371,983 B1* | 4/2002 | Lane ......................... 623/2.14 |
| 6,413,275 B1 | 7/2002 | Nguyen et al. |
| 6,454,799 B1 | 9/2002 | Schrek |
| 6,461,382 B1 | 10/2002 | Cao |
| 6,530,952 B2 | 3/2003 | Vesely |
| 6,558,418 B2 | 5/2003 | Carpentier et al. |
| 6,716,244 B2 | 4/2004 | Klaco |
| 2002/0138138 A1 | 9/2002 | Yang |
| 2003/0023302 A1 | 1/2003 | Moe et al. |

FOREIGN PATENT DOCUMENTS

| | | |
|---|---|---|
| WO | WO 01/76510 A2 | 10/2001 |

* cited by examiner

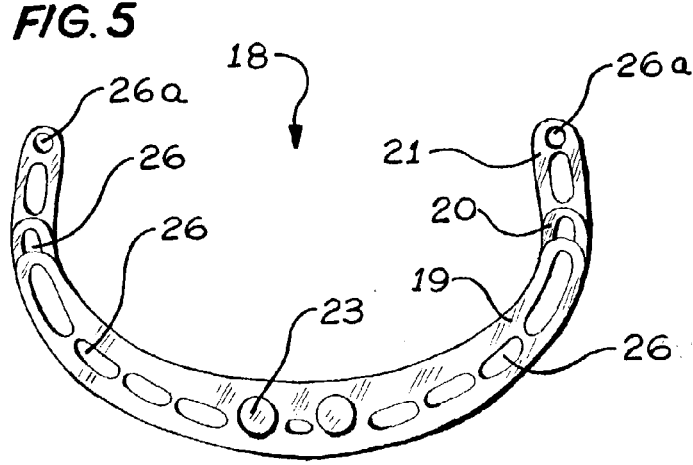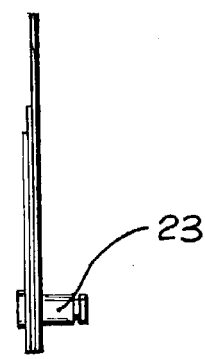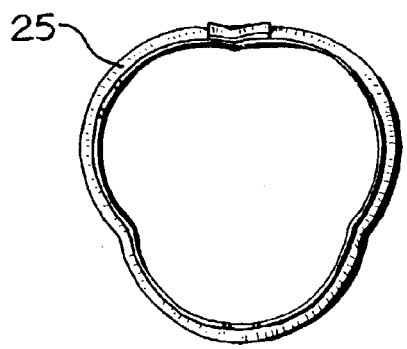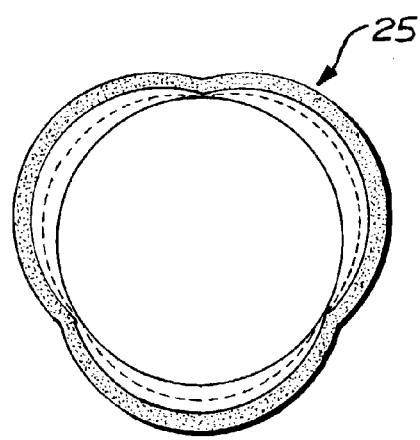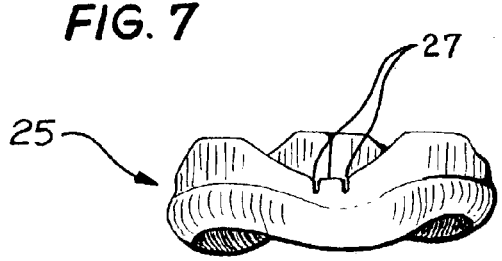

FIG.17
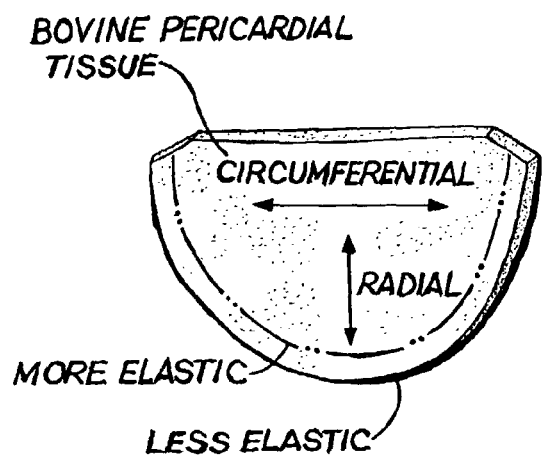
FIG.17A
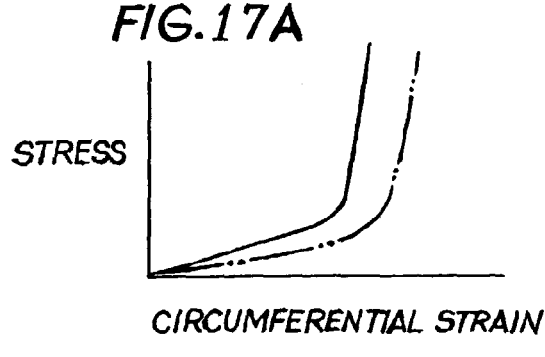
FIG.17B
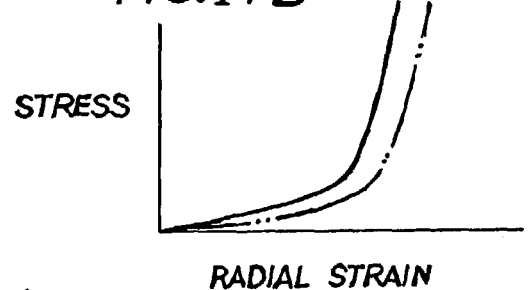
FIG.18A
"PRIOR ART"
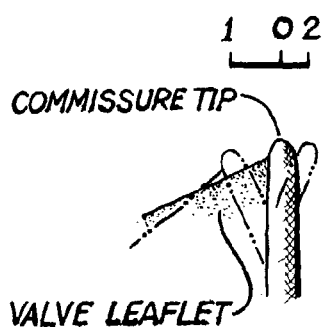
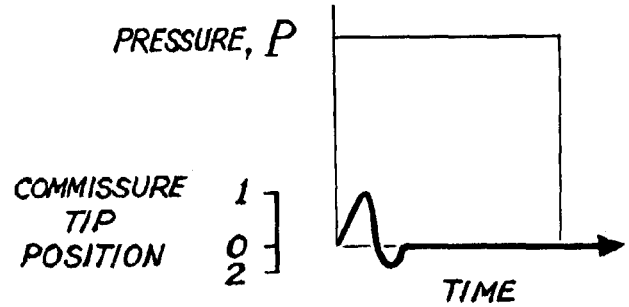
FIG.18B
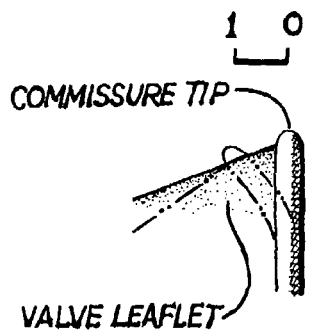
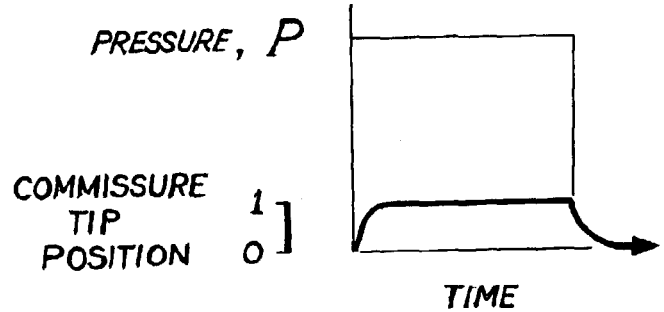

BIOPROSTHETIC HEART VALVE

This application claims priority from my International Application Ser. No. PCT/US 01/49618, filed Dec. 27, 2001, the disclosure of which is incorporated herein by reference.

The present invention relates to a biological prosthetic heart valve intended as a replacement for patients with defective heart valves and more particularly to one that can be advantageously made using bovine pericardial tissue.

BACKGROUND OF THE INVENTION

Biological tissue heart valves have evolved into several specialized designs to satisfy the on-going need of patients for a valve that will be free from structural failures and will last for the life of the adult. The primary focus of new designs for such valves has been to significantly increase the mechanical as well as the biological durability of the valve. In addition to the foregoing, these valves should be easy for surgeons to implant without any distortion and with consistent results, and the sewing ring design for an aortic valve should be compliant to accommodate both the calcific annulus as well as the annulus of a bicuspid valve.

Overall, tissue valves are still being sought that meet the following objectives: (1) low stresses at the coaptation surface of the leaflets in the closed position; (2) synchronous and symmetrical leaflet motion; (3) wrinkle-free leaflets at all phases of leaflet motion; (4) even alignment of the free margins of the tissue; and (5) hemodynamic efficiency from a trefoil stent design for the aortic position.

SUMMARY OF THE INVENTION

The present invention provides a bioprosthetic heart valve comprising a thin rigid outer frame which supports three elastic, laminated inner frames. Each inner frame comprises lamination in the form of thin crescent-shaped strips of elastic spring metal fastened together with one or more metal pins. A thin fabric covers over such inner frame structures for host tissue overgrowth and leaflet attachment. A tethered attachment between inner frames eliminates the possibility of leaflet tissue abrasion. Each free-standing inner frame provides a precise and consistent geometric positioning for one leaflet, and each is preferably designed with non-linear spring characteristics for symmetrical and synchronous leaflet motion. Such a laminated structure is able to decrease stresses at the commissure and coaptation zone without resulting in valve prolapse.

An aortic valve may have an outer frame that is trefoil-shaped in its horizontal aspect and scalloped in its axial aspect for supra-annular placement. The mounting diameter of the valve is generally measured as approximating a circle which includes the three commissure locations and goes through the three cusps of the trefoil. The outer frame is preferably made of metal that has been stiffened by increasing the section modulus through stretch-forming. To provide precision in positioning the three inner frames which support the stand-alone leaflets, slots are machined after the outer frame is formed. Both the inner and outer frames are covered with a polymeric fabric or sheet material for fastening purposes and to provide for tissue ingrowth as well known in this art, see U.S. Pat. No. 5,037,434.

An outer frame for a mitral valve is preferably circular in its inflow aspect and preferably has an oblong D-shape in the outflow aspect. Such a mitral valve may be designed to be implanted subannularly relative to the existing mitral valve so as to reside in the left atrium cavity. The valve is preferably designed so that the inflow plane of the valve housing will be tilted from 15 to 25° from the outflow plane to obtain a better transition from such a circular inflow entrance to an oblong outflow exit. Bulges similar to the sinus of Valsalva will preferably be incorporated into the housing to reduce leaflet stresses during valve opening.

For such a subannular implantation, a bovine pericardial tissue skirt is preferably sewn to encircle the inflow end or nozzle, with the opposite edge of such skirt being attached to the left atrium to make an artificial floor. Polymeric elastomeric encircling cushions are preferably attached at both ends of the valve housing to absorb transient pressure loadings and provide a buttress for suture attachments.

BRIEF DESCRIPTION OF THE DRAWINGS

FIG. 5 is a front view of an inner frame laminate with anchoring pins installed.

FIG. 5A is a side elevation view of FIG. 5.

FIGS. 6 and 7 are a top plan view and a side elevation view of the stretch-formed outer metal frame.

FIG. 8 is a plan view of the aortic valve stent outer frame having the aortic valve annulus diameter superimposed thereupon.

FIG. 17 is a perspective view of a section of bovine pericardial tissue that has been cut to the shape of a leaflet for use in a valve embodying various features of the invention.

FIGS. 17A and 17B are stress/strain curves for the tissue taken in transverse directions.

FIGS. 18A and 18B are schematic and graphical representations showing the functioning of a flexible prior art stent compared to the elastic stent embodying features of the present invention.

DETAILED DESCRIPTION OF THE PREFERRED EMBODIMENTS

A visionary hemodynamically flow-efficient bovine pericardial heart valve has been designed. The valve structure is of a self-supporting, laminated structural design that reduces the localized high stresses generated at the tips of the commissures during valve closing; the soft tips of the structure deflect only locally causing stress at the commissures to be reduced. In addition, the self-supporting, elastic structure provides a consistent and repeatable elastic spring rate (spring rate equals force divided by the deflection).

The valve assembly is composed of primarily three components, namely: (1) leaflet tissue, (2) a plurality of laminated elastic inner frames, and (3) a supporting outer frame having an attached sewing ring.

Biological variations in leaflet tissue are minimized and eliminated so far as possible. Leaflet tissue is treated with a calcification-mitigation cross-linking agent, and tissue leaflets are precisely matched with respect to their principal strain orientation and magnitude in order to essentially eliminate midterm failures. The leaflet tissue is kept free of excessive stresses that might result from elasticity and shape mismatches, distortion and wrinkles, or from the structural design itself. Precise alignment of the leaflets at their free margin plane in the closing phase of the valve is obtained through a close matching of the leaflet elasticity and principal strain direction.

To achieve significant stress reduction of the leaflets, especially at the commissural area, it has been found that a stent should preferably have elasticity close to that of the tissue, at least within an order of magnitude. The difference in the elasticity between that of the stent and that of the leaflet tissue gives rise to the level of stress gradient in the tissue. Because a high stress gradient in the closed leaflet tissue has an adverse impact on the durability of the valve, an effort is made to reduce the level of stress gradients within the leaflets. At the same time, a commissural tip of a stent should not bend excessively inward during valve closing lest there be valve prolapse or bunching of the leaflet edges at the center of the valve. It has been found that freedom of minute movements of the leaflet tissue at the anchoring line will eliminate many stresses and folds and wrinkles of the leaflets during valve opening and closing phases.

Hemodynamic efficiency of the valve in the aortic position is obtained by a trefoil stent design which enables the valve to be supra-annularly implanted, thus placing most of the stent in the sinus Valsalva space. This design particularly improves the hemodynamic performance of the smaller sizes of the aortic valves (e.g. 19 and 21 mm).

Figure 1:
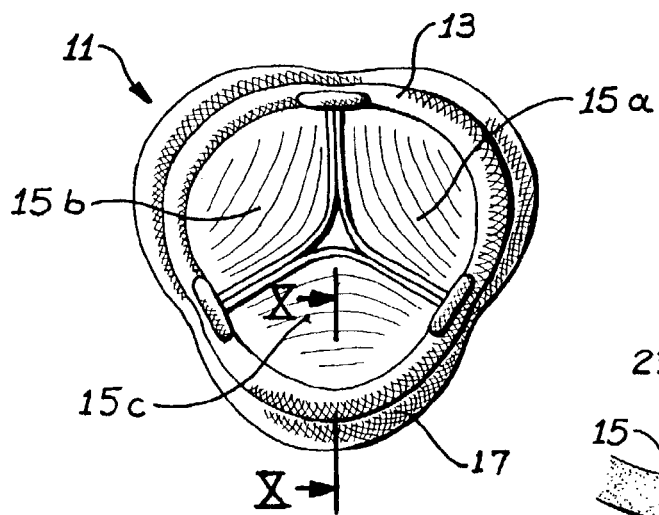
FIG. 1 is a planar view of an aortic bioprosthetic heart valve embodying various features of this invention viewed from the outflow end with the leaflets in the closed position.

Illustrated in FIG. 1 is a bioprosthetic heart valve 11 which includes a frame 13 that supports three identical valve leaflets 15 (which are labeled 15a, 15b and 15c in FIG. 1) and a sewing ring 17. In the embodiment illustrated, the sewing ring 17 is scalloped, as it might preferably be for an aortic valve. Each valve leaflet 15 is made from pericardial tissue or other appropriate synthetic polymeric fabric; however, they are preferably made from bovine pericardium. As best seen in FIGS. 3 through 7, the frame 13 includes three separate inner frame assemblies 18 which are laminates of three flat pieces of thin metal spring material of complementary shape; these three inner frame laminates are individually attached to an annular outer frame or annulus 25. The outer frame 25 supports the three inner frames 18 which in turn support the three leaflets in stand-alone fashion.

The outer frame 25 may be constructed from various suitable biocompatible materials, such as plastic or metal. The outer frame 25 (see FIGS. 6 and 7) is preferably stretch-formed from a thin piece of annealed Elgiloy about 8 mils thick or an equivalent cobalt or other metal alloy or from a superplastically formed titanium tube. The geometry of the outer frame is a three-lobe shaped structure which is sometimes referred to as having a trefoil shape. When implanting an aortic valve of such design, a segment of the frame 25 will be placed in the sinus of Valsalva cavity, away from the orifice area. The cross section of the aortic sewing ring 17 need not be constant, but it will preferably be scalloped, having curved surfaces and a shape generally like that of a casting of the sinus of Valsalva.

Each inner frame 18 (see FIG. 5) is a crescent-shaped strut in the form of a laminated structure of thin strips 19, 20, 21 of biocompatible, spring-tempered alloy metal, e.g. Elgiloy about 2 mils thick. The metal strips, which may be three or more in number, are of different lengths to create a layered lamination. Only the strip 21 extends to the tips, so there is only a single layer of metal at the tip section; this provides an elastic structure at the commissure that both reduces tensile stresses in the leaflet and minimizes whiplashing at the start of closing, as explained hereinafter with reference to FIGS. 18A and 18B. In order to provide reproducible geometry and spring rate, the inner frames 18 are affixed to the outer frame without any forming after the apertures 26, which are generally oval in shape except for the end apertures 26a which are circular, have been created, as by chemical milling. Although the three strips 19, 20 and 21 are not deformed from their flat shape, they may be spot-welded together at a central location so they will always retain the alignment shown in FIG. 5 to facilitate their handling, as during the attachment of the leaflets and their subsequent mounting in the outer frame 25.

Figure 4:
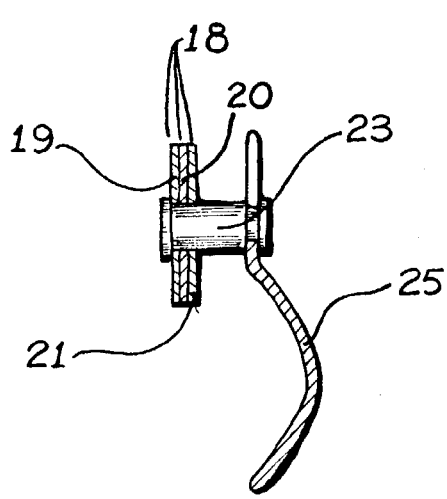
FIG. 4 is a sectional view similar to FIG. 3 with the cloth covering and valve leaflets removed.
Figure 4A:
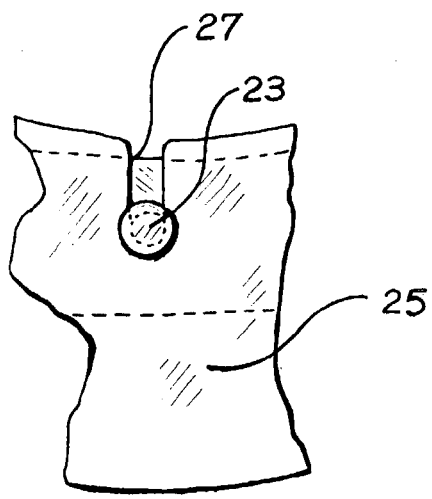
FIG. 4A is a fragmentary elevation view of FIG. 4.

The three inner frame laminates 18 are attached to the outer frame 25 through the use of anchoring pins 23 as best seen perhaps in FIGS. 4, 4A and 5A. To accommodate these anchoring pins 23, the outer frame 25 is machined with pairs of slots 27 (see FIG. 7) which are dimensioned to receive the necked-down sections of the pins as shown in FIG. 4. These machined slots 27 are located along the rim of the outer frame 25 so as to precisely position the three inner frame laminates 18 at equi-angularly spaced-apart locations thereon.

The valve leaflets 15 will be precisely cut from mammalian tissue, preferably bovine pericardium tissue, mechanically, as by a blade, or hydraulically, as by a high pressure water jet, e.g. 15,000 psi. Before cutting, the tissue is measured for its inherent resistance to stress and elongation, for pericardium tissue generally has an inherent "grain", i.e. greater resistance to stress or elongation in one direction as opposed to the transverse direction. It has been found it is advantageous for the bovine pericardium tissue that is employed be tested and then oriented prior to cutting the leaflets so that the resistance to stretching in the circumferential direction, as shown in FIG. 17, will be greater than the resistance to stretching in the radial direction. Conceivably, such resistance to stretching may be about 10% to about 50% greater; however, more usually, tissue will be chosen having a resistance to stretching in the circumferential direction that is about 10% to about 25% greater. Perhaps more importantly, tissue is tested, sorted and then matched so that all three leaflets for fabricating a single valve, either aortic or mitral, are made of tissue having about the same resistance to stretching in the circumferential direction, i.e. within about 10% of one another or preferably within about 5% of one another. The rough side of the leaflets 15 is aligned facing the inflow side, and a biased cut cloth is sewn to the arcuate edge of the leaflets.

Bovine pericardial tissue leaflets will be sorted and matched by a biomechanical-video-computer system. Each leaflet will be coded using a bar-coding system for serialization and traceability. To minimize toxicity, the valve leaflets are preferably treated with a non-glutaraldehyde solution for fixing and imparting calcification-resistance.

Figure 3:
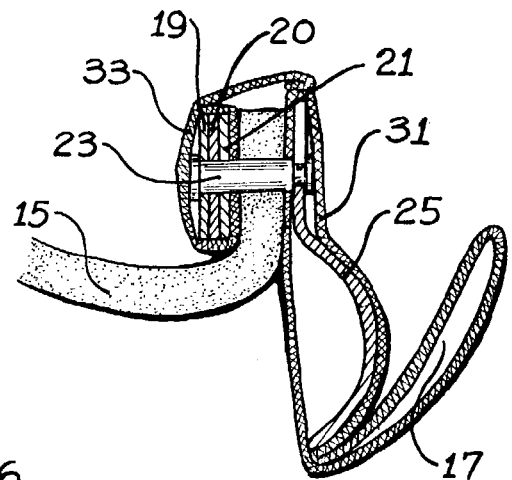
FIG. 3 is an enlarged, fragmentary sectional view taken along X—X of FIG. 1, with valve leaflets closed.
Figure 16:
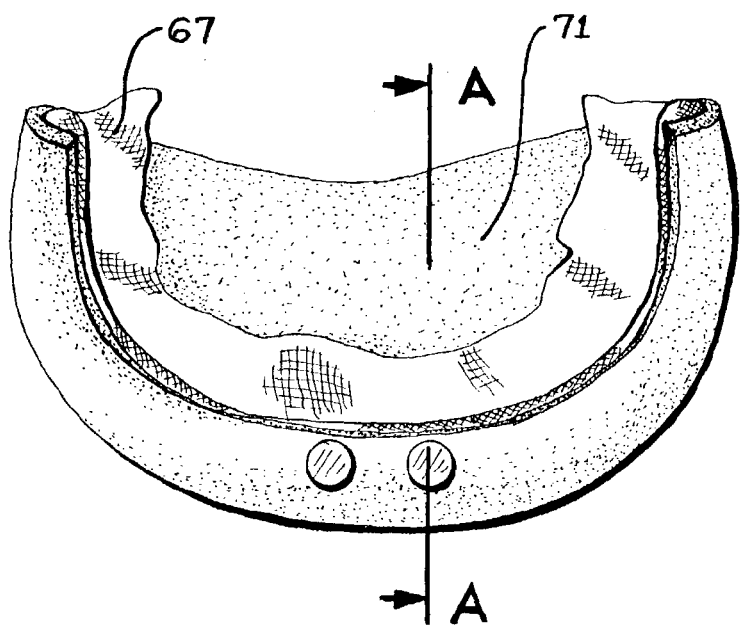
FIG. 16 shows a leaflet mounted on an inner frame member ready for assembly to the outer frame of a mitral valve.

As well known in this art, the outer frame 25 is completely covered in cloth 31, a major section of which cloth may be gathered to construct the sewing ring 17, as best seen in FIG. 3. The three inner frame laminates 18 are also completely covered with cloth 33. Such cloth covering of metal components in bioprosthetic valves is well known in this art and disclosed for example in my earlier '434 patent. The bovine pericardial leaflet tissue, after cutting and sorting, is sewn onto the cloth 33 of the inner frame along the entire underside of the crescent-shaped frames. The edge of each leaflet may be lined up evenly or at a constant offset from the inside edge of the inner frame, as best seen in FIG. 16. With the section of the cloth sewn to the leaflet, the cloth and the leaflet itself are punctured at two locations so they can be fit over and onto the anchoring pins 23 after these pins have been press-fit into the laminated inner frames 18 and become affixed thereto.

The elastic frame 18 will flex during every cardiac cycle and acts as a self-supporting laminated leaf spring. The edge that comes into contact with the leaflet has a generally elliptical curve as seen in FIG. 5. The structural requirement and the geometry of apertures 26 that are provided in the laminated structure are determined through finite element stress analysis (FEA) and pulsatile flow studies, as known in this art.

In a valve with all three leaflets opening and closing with repeatable and synchronous motion, the dimensions of the leaflet pattern may be different for tissue with different elasticities (FIG. 17). The tips of the inner frames 18 are loosely connected together, e.g. tethered with a suture or a thin cord 35 or other interconnection, which is looped through the circular apertures 26a. A cloth covering 36, broken away in FIG. 2, somewhat loosely surrounds the entire stent to minimize bending forces at the anchoring pins (See FIG. 2).

The foregoing description with regard to the structure of the inner frame laminates and the leaflets and their assembly and mounting within an outer frame is generally applicable to the construction of both aortic valves and mitral valves. However, the preferred embodiments of aortic valves and mitral valves differ, as can be seen by comparing FIGS. 1 and 2 with FIGS. 9 and 10, as explained in detail hereinafter.

As previously mentioned, the aortic outer frame 25 (FIG. 6) is a trefoil-shaped structure that is preferably coldworked, i.e. stretch-formed from a thin metal cylinder that may be either seamless or welded. The valve size is determined by the diameter of a near-circle circumscribed through the three points of the cusps of the trefoil (see dotted line near-circle in FIG. 8). The outer frame 25 is preferably stiffened by forming a bead around the structure, and it has a scalloped shape (FIG. 7) that approximates the profile of the natural aortic annulus line.

Figure 9A:
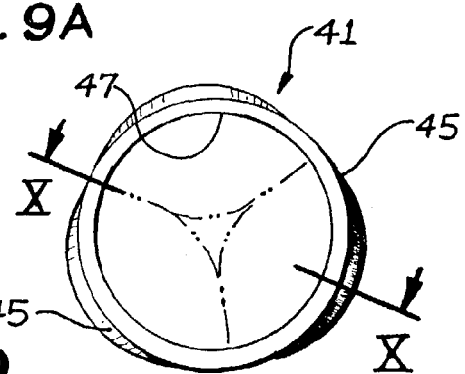
FIG. 9A is a view looking into the inflow end of the valve of FIG. 9 with the leaflets shown in dotted outline.
Figure 9:
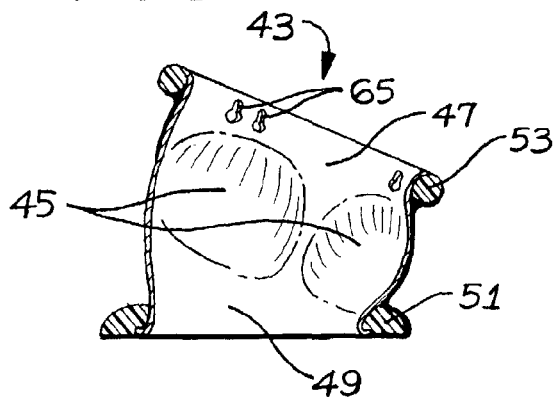
FIG. 9 is a side cross-sectional view of a mitral valve housing showing the orientation of the inflow and outflow planes.
Figure 10:
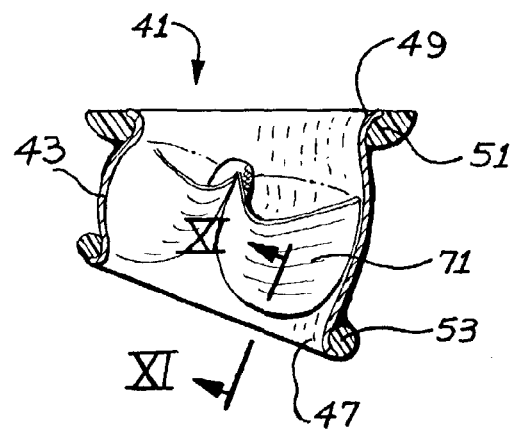
FIG. 10 is a cross-sectional view taken generally along line X—X of FIG. 9A, with the valve leaflets closed.
Figure 9B:
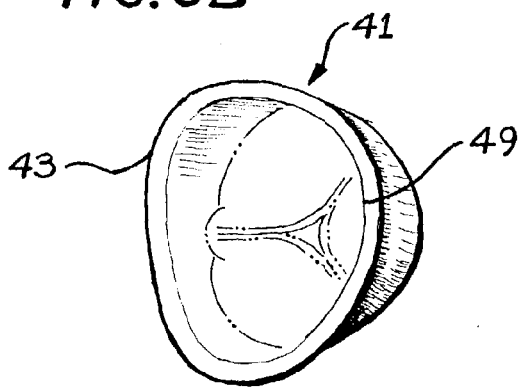
FIG. 9B is a perspective view looking at the outflow end of the valve of FIG. 9A.
Figure 15:
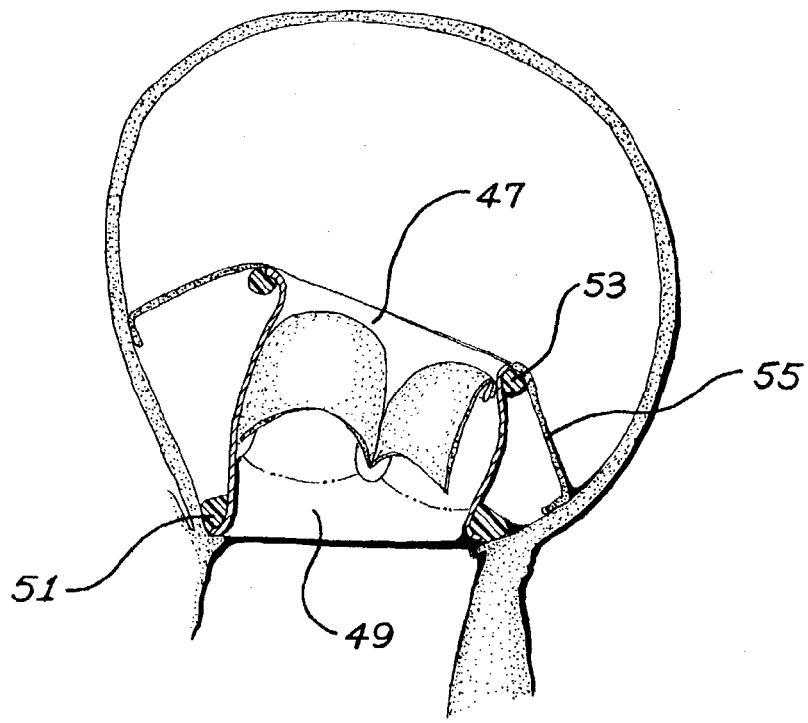
FIG. 15 is a cross-sectional view schematically showing how the mitral valve of FIGS. 9–14 may be implanted in a patient.

A mitral valve 41 has the same mechanism as the aortic valve 11 but, in its preferred form, has a housing or annulus that is different from the outer frame 25. As best seen in FIG. 9, a housing or annulus 43 is provided in the form of a metal sleeve within which the leaflets will be completely laterally enclosed. The housing 43 is preferably fabricated from stretch-formed biocompatible metal, such as that specified for the outer frame of the aortic valve, e.g. Elgiloy Co—Cr—Ni alloy having a thickness of about 8 mils, (0.2 mm); however, it might be made of the other materials mentioned hereinbefore. The housing is formed with the addition of three cavities or bulges 45 that approximate the sinus of Valsalva, which has been found to reduce stresses in the leaflets. An entrance or inflow end 47 and a exit or outflow end 49 of the housing are planar and are oriented at an angle of between about 15° and about 25° to each other, as illustrated in FIG. 9. The entrance end 47 is generally circular (see FIG. 9A), whereas the exit end has an oblong D-shape (see FIG. 9B) which is generally similar to the shape of a natural mitral valve annulus. The valve 41 is designed for implantation subannularly in the left atrium cavity (see FIG. 15), and a sewing ring 51, preferably of elastomeric material, is provided encircling the exit end 49 of the housing for suturing therethrough to implant the valve between the atrium and the ventricle. This design for such a subannularly implantable mitral valve eliminates potential problems associated with the possible puncturing of the left ventricle wall by a valve strut and possible resultant obstruction in the outflow channel.

In this preferred embodiment, a second elastomeric ring 53 encircles the inflow end 47 of the housing and is used to mount a large ring-shaped piece 55 of pericardial tissue (FIG. 15) which serves as a skirt that entirely surrounds the implanted valve. The smaller diameter perimeter of the ring-shaped tissue 55 is sutured to the elastomeric sewing ring 53 at the inflow end 47 of the housing 43, and the outer perimeter of the skirt is trimmed by the surgeon and sutured onto the wall of the left atrium to form a new floor for the left atrium cavity after the valve 41 has been implanted by suturing the outflow sewing ring 51 onto the annulus of the excised mitral valve (see FIG. 15). These sewing rings 51, 53 may be made of any suitable biocompatible silicone elastomer or polymeric equivalent as is well known in this art. As previously mentioned, rings of such material are effective to absorb transient pressure loadings.

Figure 11:
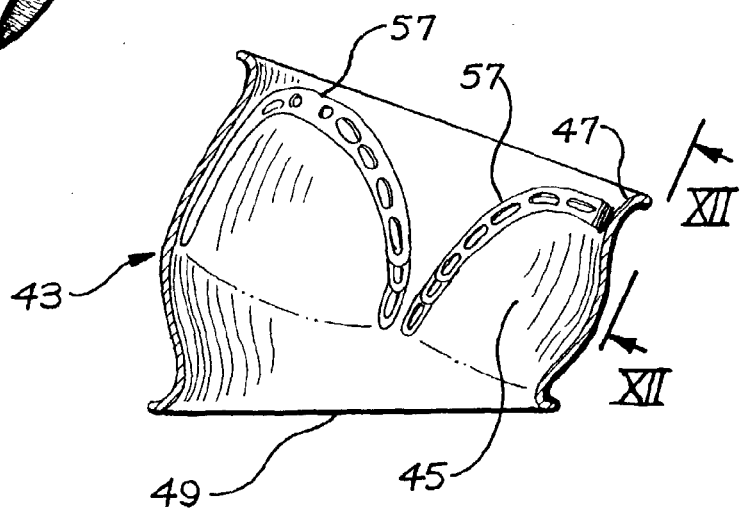
FIG. 11 is a cross-sectional view similar to FIG. 9, with the inner frame in place and shown in elevation without its cloth covering or the leaflet tissue.
Figure 14:
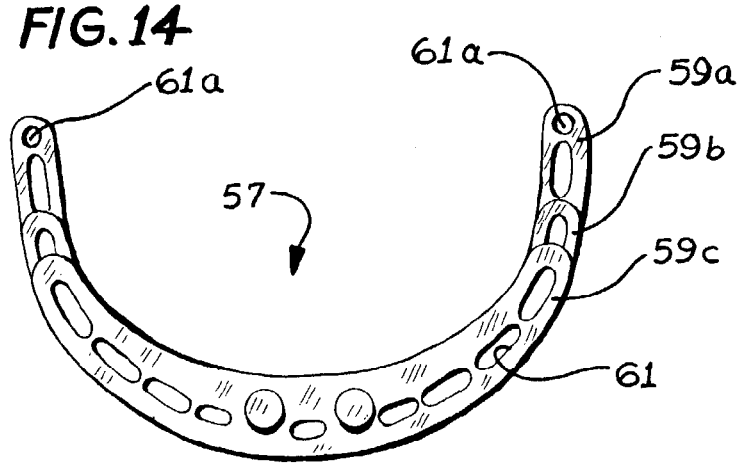
FIG. 14 is a front view similar to FIG. 5 of an inner frame laminate for the mitral valve.

As mentioned before, the structure of the operating mechanism of the mitral valve 41 is essentially the same as that described for the aortic valve 11. As seen in FIG. 11, three laminated struts 57 are appropriately mounted within the housing 43 so as to generally be aligned with the outlines of the three bulges 45 that were formed to approximate the sinus of Valsalva. As best seen in FIG. 14, the struts 57 are generally crescent-shaped, but their shape may more closely resemble that of a U. They are similarly constructed of three thin strips 59a, 59b, 59c and are of varying length; they contain a series of oval apertures 61 that are sized so as to provide the desired elasticity and also to allow biocompatible cloth to be stitched in surrounding relation to the laminated struts. Circular apertures 61a are provided near the tips for the loose tethering as in the case of the apertures 26a. The three thin flat pieces or strips 59 that make up the strut 57 are interconnected in a central region by a pair of anchoring pins 63 that have a head at one end and a diameter just slightly larger than that of two circular holes formed in the three pieces, so that a press-fit results which affixes the pins to all three of the pieces and thus interconnects the pieces to one another. If desired to facilitate the overall assembly of the valve, the three pieces 59 may be preliminarily spot-welded, as for example at a central location between the two holes that receive the pins 63, so as to facilitate the assembly by allowing the lamination to be handled as a single entity.

As a result of this strut construction, the three pieces 59 of metal spring material are free to move radially inward toward the center of the valve housing 43 independent of movement of the adjacent piece, at least within the confines of the surrounding envelope provided by overwrapped biocompatible cloth; such movement occurs during the closing of the valve. It thus allows a desired soft spring constant to be achieved which will be consistent and reproducible in these stand-alone individual leaflet supports. On the other hand, when the pressure keeping the valve leaflets closed is relieved so that the strut ends move radially outward, the other two pieces 59b and 59c of the lamination will dampen the momentum that the ends of the piece 59a will have to continue to move radially outward and thus overcome any tendency they may have to move past the plane of the strut at these end locations (see FIGS. 18A and 18B), which are generally referred to in tissue valves of this type as the commissures.

Figure 12:
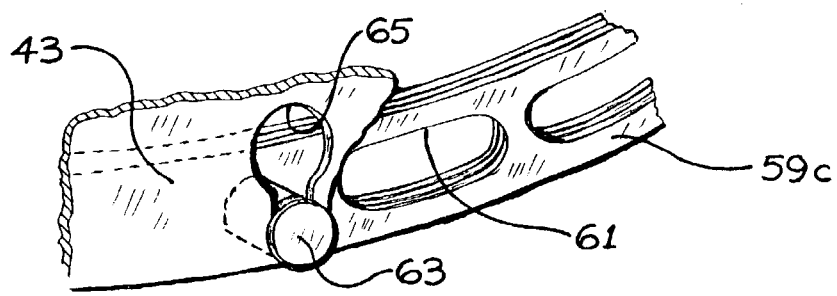
FIG. 12 is a fragmentary enlarged perspective view looking alone line XII—XII of FIG. 11, but inverted, and showing an anchoring pin for attaching an inner frame to the outer frame.
Figure 13:
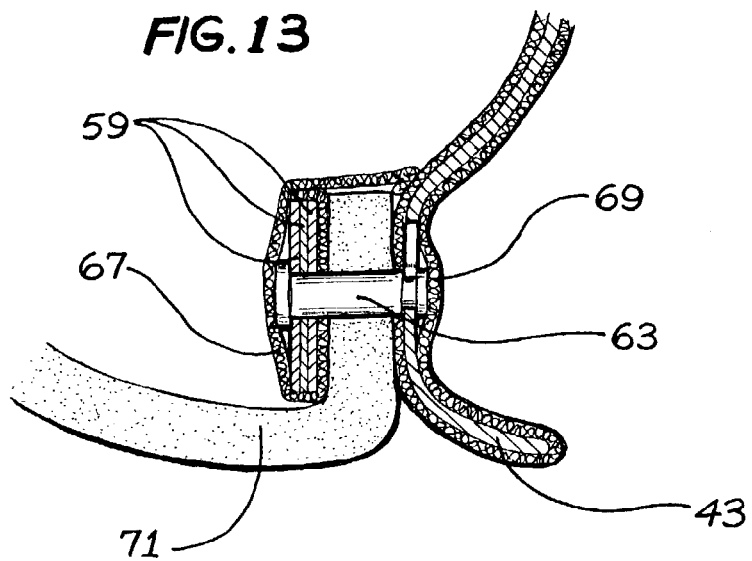
FIG. 13 is a fragmentary sectional view similar to FIG. 3 showing the tissue attachment.
Figure 14A:
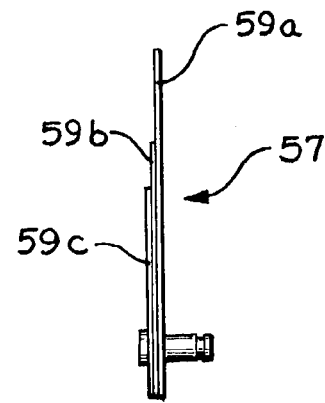
FIG. 14A is a side elevation view of FIG. 14.

As best seen in FIG. 14A, the anchor pins 63 are provided with reduced diameter neck portions near the opposite end which are then mounted in the housing 43 via keyhole slots 65 that are provided therein adjacent the entrance end of the housing, as best seen in FIGS. 9 and 12. The dimensioning of these slots 65 is such that a press-fit occurs between the neck of the anchor pin 63 and the smaller section of the keyhole slot; it results in affixation of the U-shaped strut or inner frame 57 to the housing. As best seen in FIG. 13, the three strips 59 that form the laminated strut are wrapped in biocompatible cloth 67 that can be joined, if desired, to biocompatible cloth 69 that is wrapped about the housing.

Figure 2:
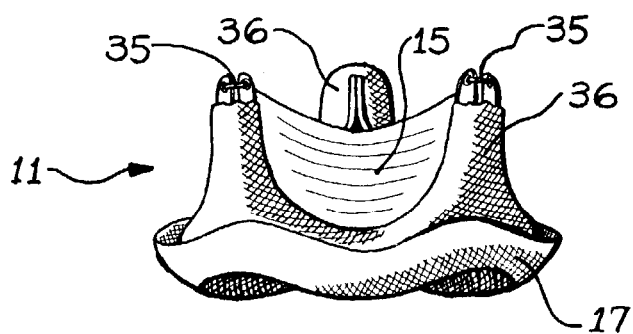
FIG. 2 is a side elevation view of FIG. 1 with the cloth covering broken away from two of the three commissures.
Figure 16A:
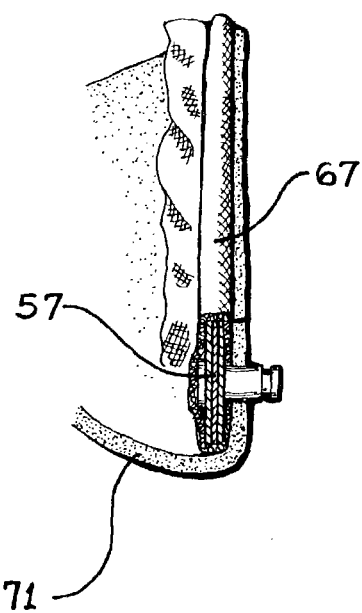
FIG. 16A is a cross-sectional view taken generally along the line A—A of FIG. 16.

As previously mentioned, leaflets 71 are cut from tissue, sorted and graded as per the aortic valves. As a part of the assembly operation, the cut tissue for fashioning a leaflet 71 for the mitral valve 41 is aligned with the edge of the U-shaped laminated inner frame or strut 57. As best seen for example in FIGS. 16 and 16A, the laminated inner frame 57 is wrapped in cloth 67 prior to attachment of the leaflet 71 thereto. The edge of the tissue is aligned with the outer surface of the cloth-covered strut 57, and it is attached thereto via suturing. This alignment extends from one tip of the crescent-shaped strut 57 to the other, and the tissue 71 is punctured at two locations to allow passage of the anchoring pins 63 therethrough. Once the tissue that constitutes the leaflet 71 has its surface juxtaposed with the outer facing surface of the cloth-wrapped strut, the edge margin of the tissue is sewed to the cloth 67 to effect the attachment of the tissue leaflets to the supporting U-shaped struts. As a result, it can be seen that each of the leaflets 71 constitutes a free-standing structure, the movement of which is guided by the elastic U-shaped inner frames 57, and movement is not directly dependent upon movement of the two flanking leaflets. Because of the laminated structure made of strips of different lengths, the struts have nonlinear spring characteristics. However, inasmuch as the intention is for all of the three leaflets 71 to operate in substantial unison, the tips of adjacent U-shaped struts are loosely tethered to each other, as by tying a thin cord of suture material or the like into a loop through the apertures 61 a at these locations which constitute the three commissures of the valve. Such tethering is illustrated in FIG. 2 and identified by the reference numeral 35.

Although the invention has been illustrated with regard to certain preferred embodiments which constitute the best mode presently known to the inventor for carrying out the invention, it should be understood that various changes and modifications as would be obvious to one having the ordinary skill in this art may be made without departing from the scope of the invention which is defined in the claims appended hereto. For example, U.S. Pat. No. 5,928,281 shows alternative methods for wrapping fabric about elements in a tissue-type heart valve. The disclosures of all U.S. patents mentioned herein are expressly incorporated herein by reference.

The invention claimed is:

1. A replacement tissue heart valve, which valve comprises an annulus having a central passageway, three generally crescent-shaped struts connected generally near the midpoints thereof to said annulus at angularly spaced locations therealong, three separate biocompatible flexible leaflets respectively attached to one of each of said struts in locations so as to converge toward one another to close said passageway and to thereafter diverge therefrom to reopen said passageway, each of said leaflets being supported as a stand-alone unit which moves independently of other said leaflets, and said annulus and said struts being covered with biocompatible fabric, wherein said struts are connected by anchor pins to said annulus, which pins pass through a marginal portion of said leaflet that is attached to said crescent-shaped strut.

2. The heart valve according to claim 1 wherein adjacent leaflets are loosely tethered to one another at locations adjacent the ends of said struts and otherwise remain free to move independently.

3. The heart valve according to claim 1 wherein said leaflets are sections of bovine pericardial tissue.

4. The heart valve according to claim 3 wherein said tissue is oriented so as to have a resistance to stress and elongation in the circumferential direction at least about 10to 20% greater than its resistance in the radial direction.

5. The heart valve according to claim 1 wherein said annulus is trefoil-shaped in plan and has an axial profile that is scalloped-shaped at the inlet entrance thereto.

6. The heart valve according to claim 5 wherein said annulus is formed from a cobalt-chromium-nickel alloy strip that is welded into circular form and then stretch-formed in a die to create said trefoil and scalloped shape.

7. The heart valve according to claim 1 that is designed for replacement of a mitral valve wherein said annulus has a generally planar entrance end and a generally planar exit end, which planes are oriented at an angle from about 15° to about 25° to each other.

8. The heart valve according to claim 7 wherein the shape of said entrance end of said annulus is generally circular and wherein said exit end of said annulus has of a generally oblong D-shape.

9. The heart valve according to claim 7 wherein elastomeric polymeric rings are affixed to the exterior surface of said annulus at each of said entrance and exit ends which serve as sewing rings and cushion the valve from the remainder of the heart.

10. The heart valve according to claim 9 which is designed to be implanted subannularly in the left atrium cavity, wherein a bovine pericardial tissue skirt surrounds said entrance end, which skirt is proportioned to be attached to the wall of the left atrium to establish an artificial floor therein surrounding the implanted valve.

11. A replacement tissue heart valve, which valve comprises an annulus having a central passageway, three generally crescent-shaped struts connected generally near the midpoints thereof to said annulus at angularly spaced locations therealong, three separate biocompatible flexible leaflets respectively attached to one of each of said struts in locations so as to converge toward one another to close said passageway and to thereafter diverge therefrom to reopen said passageway, each of said leaflets being supported as a stand-alone unit which moves independently of other said leaflets, and said annulus and said struts being covered with biocompatible fabric, wherein each of said crescent-shaped struts is made from a plurality of pieces of biocompatible metal spring material of sheet form, which individual pieces are juxtaposed with one another as a lamination.

12. The heart valve according to claim 11 wherein said individual pieces of said lamination are physically interconnected to one another within a central region thereof.

13. The heart valve according to claim 12 wherein said laminated crescent-shaped struts include at least three separate crescent-shaped pieces, each of which is of a different length.

14. The heart valve according to claim 11 wherein said laminated crescent-shaped struts have nonlinear spring characteristics which create symmetrical and synchronous leaflet motion.

15. A bioprosthetic heart valve, which valve comprises an annulus having a central passageway, three generally crescent-shaped struts connected generally near the midpoints thereof to said annulus at angularly spaced locations therealong, and three separate biocompatible flexible leaflets respectively attached to one of each of said struts in locations so as to converge toward one another to close said passageway and to thereafter diverge therefrom to reopen said passageway, each of said crescent-shaped struts acting as a self-supporting leaf spring, wherein said crescent-shaped struts include a laminate structure of multiple pieces, each of which is of a different length and wherein said laminated structure has nonlinear spring characteristics which create symmetrical and synchronous leaflet motion.

16. The heart valve according to claim 15 wherein adjacent of said pieces having said greatest length are loosely tethered to one another at locations near the tips thereof.

* * * * *